United States Patent [19]
Fukui et al.

[11] Patent Number: 5,719,026
[45] Date of Patent: Feb. 17, 1998

[54] METHOD FOR DETECTING POLYMORPHISM OF HUMAN CYTOCHROME P4501A2 GENE

[75] Inventors: Takafumi Fukui; Kiyonori Katsuragi; Moritoshi Kinoshita, all of Tokushima; Sadahito Shin, deceased, late of Tokushima, all of Japan, by Sadae Kim, heiress

[73] Assignee: Otsuka Pharmaceutical Co., Ltd., Tokyo, Japan

[21] Appl. No.: 605,089

[22] PCT Filed: Jul. 6, 1995

[86] PCT No.: PCT/JP95/01352

§ 371 Date: Mar. 6, 1996

§ 102(e) Date: Mar. 6, 1996

[87] PCT Pub. No.: WO96/01328

PCT Pub. Date: Jan. 18, 1996

[30] Foreign Application Priority Data

Jul. 6, 1994 [JP] Japan .................... 6-154571

[51] Int. Cl.$^6$ .................... C12Q 1/68; C12P 19/34; C07H 21/04; C12N 15/00
[52] U.S. Cl. .................... 435/6; 435/91.1; 435/91.2; 536/23.5; 536/24.31; 536/24.33; 935/8; 935/14; 935/77; 935/78
[58] Field of Search .................... 435/6, 91.1, 91.2, 435/183; 536/23.1, 23.5, 24.31, 24.33; 935/8, 14, 77, 78

[56] References Cited

FOREIGN PATENT DOCUMENTS 5-503845  6/1993  Japan .................. C12Q 1/68
5-211895  8/1993  Japan .................. C12Q 1/68

OTHER PUBLICATIONS

Botsch et al., "Identification and Characterization of the Cytochrome P450 enzymes involved in N–dealkylation of Propafenone: Molecular Base for Interaction Potential and Variable Disposition of Active–Metabolites," Molecular Pharmacology, vol. 43, No. 1, 1993.

Analytical Biochemistry, vol. 222, No. 1 1994 (94), B.B. Rasmussen (Determination of theophylline metabolites in human liver microsomes by high–performance liquid chromatography) pp. 9–13.

Molecular Pharmacology, vol., 43, No. 1 1993 (93), S. Botsch (Identification and characterization of the cytochrome P450 enzymes involved in N–dealkylation of propafenone: Molecular base for interaction potential and variable disposition of active–metabolites) pp. 120–126.

*Primary Examiner*—Bradley L. Sisson
*Attorney, Agent, or Firm*—Sughrue, Mion, Zinn, Macpeak & Seas, PLLC

[57] ABSTRACT

The present invention provides a method for detecting polymorphism of the human cytochrome P4501A2 (CYP1A2) gene in which substitution at a 2064th base, substitution at a 2640th base, and/or deletion of a −1569th base in a nontranslational region of the human cytochrome P4501A2 gene are/is detected. According to the method of the invention, new types of polymorphism of the CYP1A2 gene can be detected simply and easily with high sensitivity and accuracy, and the method requires only a small amount of a DNA sample.

14 Claims, 1 Drawing Sheet

SEQUENCE LISTING ( 1 ) GENERAL INFORMATION:

( i i i ) NUMBER OF SEQUENCES: 45

( 2 ) INFORMATION FOR SEQ ID NO: 1:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 1:

CCTCCTTTTT TCCCTGCAGT                                 20

( 2 ) INFORMATION FOR SEQ ID NO: 2:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 2:

TCATCCTTGA CAGTGCCAGG                                 20

( 2 ) INFORMATION FOR SEQ ID NO: 3:

( i ) SEQUENCE CHARACTERISTICS:
        ( A ) LENGTH: 19 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 3:

ATGTGCTGAC CCTGGGGAA                                  19

( 2 ) INFORMATION FOR SEQ ID NO: 4:

( i ) SEQUENCE CHARACTERISTICS:
        ( A ) LENGTH: 19 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 4:

GCTGAAGGTC AAGCTCTGG                                  19

( 2 ) INFORMATION FOR SEQ ID NO: 5:

( i ) SEQUENCE CHARACTERISTICS:
        ( A ) LENGTH: 19 BASES ( B ) TYPE: NUCLEOTIDE
( C ) STRANDEDNESS: SINGLE
( D ) TOPOLOGY: LINEAR ( i i ) MOLECULE TYPE: DNA ( x i ) SEQUENCE DESCRIPTION: SEQ ID NO: 5:

CCTCCACCCT CATCACTGA                                          19

( 2 ) INFORMATION FOR SEQ ID NO: 6:

( i ) SEQUENCE CHARACTERISTICS:
      ( A ) LENGTH: 19 BASES
      ( B ) TYPE: NUCLEOTIDE
      ( C ) STRANDEDNESS: SINGLE
      ( D ) TOPOLOGY: LINEAR    ( i i ) MOLECULE TYPE: DNA    ( i x ) SEQUENCE DESCRIPTION: SEQ ID NO: 6:

TGTAAGGGTC GAAGTGCCC                                          19

( 2 ) INFORMATION FOR SEQ ID NO: 7:

( i ) SEQUENCE CHARACTERISTICS:
      ( A ) LENGTH: 19 BASES
      ( B ) TYPE: NUCLEOTIDE
      ( C ) STRANDEDNESS: SINGLE
      ( D ) TOPOLOGY: LINEAR    ( i i ) MOLECULE TYPE: DNA    ( x i ) SEQUENCE DESCRIPTION: SEQ ID NO: 7:

TGCAGGAGCT GATGGCAGG                                          19

( 2 ) INFORMATION FOR SEQ ID NO: 8:

( i ) SEQUENCE CHARACTERISTICS:
      ( A ) LENGTH: 19 BASES
      ( B ) TYPE: NUCLEOTIDE
      ( C ) STRANDEDNESS: SINGLE
      ( D ) TOPOLOGY: LINEAR    ( i i ) MOLECULE TYPE: DNA    ( x i ) SEQUENCE DESCRIPTION: SEQ ID NO: 8:

CGAAGGATGG GGAAGAAGT                                          19

( 2 ) INFORMATION FOR SEQ ID NO: 9:

( i ) SEQUENCE CHARACTERISTICS:
      ( A ) LENGTH: 20 BASES
      ( B ) TYPE: NUCLEOTIDE
      ( C ) STRANDEDNESS: SINGLE
      ( D ) TOPOLOGY: LINEAR    ( i i ) MOLECULE TYPE: DNA    ( x i ) SEQUENCE DESCRIPTION: SEQ ID NO: 9:

TCATGAGTTC GTGGAGACTG                                         20

( 2 ) INFORMATION FOR SEQ ID NO: 10:

( i ) SEQUENCE CHARACTERISTICS:
      ( A ) LENGTH: 18 BASES
      ( B ) TYPE: NUCLEOTIDE
      ( C ) STRANDEDNESS: SINGLE
      ( D ) TOPOLOGY: LINEAR    ( i i ) MOLECULE TYPE: DNA ( i x ) SEQUENCE DESCRIPTION: SEQ ID NO: 10:

AAGGTGCCCC TTGCCACC                                                                 18

( 2 ) INFORMATION FOR SEQ ID NO: 11:

( i ) SEQUENCE CHARACTERISTICS:
        ( A ) LENGTH: 19 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 11:

AGTGCCAGAG TGCCCCTAA                                                                19

( 2 ) INFORMATION FOR SEQ ID NO: 12:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 12:

TGAACAGCAG GCATGTGGAT                                                               20

( 2 ) INFORMATION FOR SEQ ID NO: 13:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 13:

TCCTCACCTT ACACTACACG                                                               20

( 2 ) INFORMATION FOR SEQ ID NO: 14:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( i x ) SEQUENCE DESCRIPTION: SEQ ID NO: 14:

TGGGTTTCAA GGCTTCTCCT                                                               20

( 2 ) INFORMATION FOR SEQ ID NO: 15:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 15:

CTGCTTGTCC TCTGTGTTCT                                                               20

( 2 ) INFORMATION FOR SEQ ID NO: 16:

( i ) SEQUENCE CHARACTERISTICS:
     ( A ) LENGTH: 20 BASES
     ( B ) TYPE: NUCLEOTIDE
     ( C ) STRANDEDNESS: SINGLE
     ( D ) TOPOLOGY: LINEAR ( i i ) MOLECULE TYPE: DNA ( x i ) SEQUENCE DESCRIPTION: SEQ ID NO: 16:

TGGCAAGCAC TTTAGAGGTG                    20

( 2 ) INFORMATION FOR SEQ ID NO: 17:

( i ) SEQUENCE CHARACTERISTICS:
     ( A ) LENGTH: 19 BASES
     ( B ) TYPE: NUCLEOTIDE
     ( C ) STRANDEDNESS: SINGLE
     ( D ) TOPOLOGY: LINEAR ( i i ) MOLECULE TYPE: DNA ( x i ) SEQUENCE DESCRIPTION: SEQ ID NO: 17:

GCAACACATG CCCCAGCTT                     19

( 2 ) INFORMATION FOR SEQ ID NO: 18:

( i ) SEQUENCE CHARACTERISTICS:
     ( A ) LENGTH: 20 BASES
     ( B ) TYPE: NUCLEOTIDE
     ( C ) STRANDEDNESS: SINGLE
     ( D ) TOPOLOGY: LINEAR ( i i ) MOLECULE TYPE: DNA ( i x ) SEQUENCE DESCRIPTION: SEQ ID NO: 18:

ACTGCTGAAC CTGCACACAT                    20

( 2 ) INFORMATION FOR SEQ ID NO: 19:

( i ) SEQUENCE CHARACTERISTICS:
     ( A ) LENGTH: 20 BASES
     ( B ) TYPE: NUCLEOTIDE
     ( C ) STRANDEDNESS: SINGLE
     ( D ) TOPOLOGY: LINEAR ( i i ) MOLECULE TYPE: DNA ( x i ) SEQUENCE DESCRIPTION: SEQ ID NO: 19:

ATCTCCTGCT GTTCCTCTTG                    20

( 2 ) INFORMATION FOR SEQ ID NO: 20:

( i ) SEQUENCE CHARACTERISTICS:
     ( A ) LENGTH: 20 BASES
     ( B ) TYPE: NUCLEOTIDE
     ( C ) STRANDEDNESS: SINGLE
     ( D ) TOPOLOGY: LINEAR ( i i ) MOLECULE TYPE: DNA ( x i ) SEQUENCE DESCRIPTION: SEQ ID NO: 20:

AACTCCAGTT GCTGTAGCAG                    20

( 2 ) INFORMATION FOR SEQ ID NO: 21:

( i ) SEQUENCE CHARACTERISTICS:
     ( A ) LENGTH: 20 BASES ( B ) TYPE: NUCLEOTIDE
                ( C ) STRANDEDNESS: SINGLE
                ( D ) TOPOLOGY: LINEAR ( i i ) MOLECULE TYPE: DNA ( x i ) SEQUENCE DESCRIPTION: SEQ ID NO: 21:

CCAAGTGGGA GATCTTCCTC                                                           20

( 2 ) INFORMATION FOR SEQ ID NO: 22:

( i ) SEQUENCE CHARACTERISTICS:
                ( A ) LENGTH: 20 BASES
                ( B ) TYPE: NUCLEOTIDE
                ( C ) STRANDEDNESS: SINGLE
                ( D ) TOPOLOGY: LINEAR ( i i ) MOLECULE TYPE: DNA ( i x ) SEQUENCE DESCRIPTION: SEQ ID NO: 22:

GGAAGAGAAA CAAGGGCTGA                                                           20

( 2 ) INFORMATION FOR SEQ ID NO: 23:

( i ) SEQUENCE CHARACTERISTICS:
                ( A ) LENGTH: 20 BASES
                ( B ) TYPE: NUCLEOTIDE
                ( C ) STRANDEDNESS: SINGLE
                ( D ) TOPOLOGY: LINEAR ( i i ) MOLECULE TYPE: DNA ( x i ) SEQUENCE DESCRIPTION: SEQ ID NO: 23:

AACCAGGCCA ATCTGATAGG                                                           20

( 2 ) INFORMATION FOR SEQ ID NO: 24:

( i ) SEQUENCE CHARACTERISTICS:
                ( A ) LENGTH: 21 BASES
                ( B ) TYPE: NUCLEOTIDE
                ( C ) STRANDEDNESS: SINGLE
                ( D ) TOPOLOGY: LINEAR ( i i ) MOLECULE TYPE: DNA ( x i ) SEQUENCE DESCRIPTION: SEQ ID NO: 24:

AGCTTCCAGG TTCTATAGTT G                                                         21

( 2 ) INFORMATION FOR SEQ ID NO: 25:

( i ) SEQUENCE CHARACTERISTICS:
                ( A ) LENGTH: 20 BASES
                ( B ) TYPE: NUCLEOTIDE
                ( C ) STRANDEDNESS: SINGLE
                ( D ) TOPOLOGY: LINEAR ( i i ) MOLECULE TYPE: DNA ( x i ) SEQUENCE DESCRIPTION: SEQ ID NO: 25:

GTACCTTTCT TGGGACCAAT                                                           20

( 2 ) INFORMATION FOR SEQ ID NO: 26:

( i ) SEQUENCE CHARACTERISTICS:
                ( A ) LENGTH: 20 BASES
                ( B ) TYPE: NUCLEOTIDE
                ( C ) STRANDEDNESS: SINGLE
                ( D ) TOPOLOGY: LINEAR ( i i ) MOLECULE TYPE: DNA ( i x ) SEQUENCE DESCRIPTION: SEQ ID NO: 26:

AATGGCTTAG TCCAAACTGC                                                   20

( 2 ) INFORMATION FOR SEQ ID NO: 27:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 27:

CTACCCAGCT CTTGACTTCT                                                   20

( 2 ) INFORMATION FOR SEQ ID NO: 28:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 28:

CAGGGCATTC TTTATCAATA                                                   20

( 2 ) INFORMATION FOR SEQ ID NO: 29:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 29:

GTGAGAGGAT GGGGACTCAT                                                   20

( 2 ) INFORMATION FOR SEQ ID NO: 30:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( i x ) SEQUENCE DESCRIPTION: SEQ ID NO: 30:

GTACCAAAGA GTCCCTGCCA                                                   20

( 2 ) INFORMATION FOR SEQ ID NO: 31:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 31:

CCCTTGGGTA TATGGAAGGT                                                   20

( 2 ) INFORMATION FOR SEQ ID NO: 32:

( i ) SEQUENCE CHARACTERISTICS:
        ( A ) LENGTH: 19 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 32:

CAACATGAAC GCTGGCTCT         19

( 2 ) INFORMATION FOR SEQ ID NO: 33:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 33:

CCCAGAAGTG GAAACTGAGA         20

( 2 ) INFORMATION FOR SEQ ID NO: 34:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 34:

GGGTTGAGAT GGAGACATTC         20

( 2 ) INFORMATION FOR SEQ ID NO: 35:

( i ) SEQUENCE CHARACTERISTICS:
        ( A ) LENGTH: 22 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 35:

GAGCCTGGGC TAGGTGACGG GG         22

( 2 ) INFORMATION FOR SEQ ID NO: 36:

( i ) SEQUENCE CHARACTERISTICS:
        ( A ) LENGTH: 18 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( i x ) SEQUENCE DESCRIPTION: SEQ ID NO: 36:

GGCTGCCCTT GTGCTAAG         18

( 2 ) INFORMATION FOR SEQ ID NO: 37:

( i ) SEQUENCE CHARACTERISTICS:
        ( A ) LENGTH: 25 BASES (B) TYPE: NUCLEOTIDE
(C) STRANDEDNESS: SINGLE
(D) TOPOLOGY: LINEAR (ii) MOLECULE TYPE: DNA (xi) SEQUENCE DESCRIPTION: SEQ ID NO: 37:

AAAGACGGGG AGCCTGGGCT AGGTG                                  25

(2) INFORMATION FOR SEQ ID NO: 38:

(i) SEQUENCE CHARACTERISTICS:
    (A) LENGTH: 30 BASES
    (B) TYPE: NUCLEOTIDE
    (C) STRANDEDNESS: SINGLE
    (D) TOPOLOGY: LINEAR (ii) MOLECULE TYPE: DNA (xi) SEQUENCE DESCRIPTION: SEQ ID NO: 38:

AGCCAGGGCC AGGGCTGCCC TTGTGCTAAG                             30

(2) INFORMATION FOR SEQ ID NO: 39:

(i) SEQUENCE CHARACTERISTICS:
    (A) LENGTH: 20 BASES
    (B) TYPE: NUCLEOTIDE
    (C) STRANDEDNESS: SINGLE
    (D) TOPOLOGY: LINEAR (ii) MOLECULE TYPE: DNA (xi) SEQUENCE DESCRIPTION: SEQ ID NO: 39:

CCCAGAAGTG GAAACTGAGA                                        20

(2) INFORMATION FOR SEQ ID NO: 40:

(i) SEQUENCE CHARACTERISTICS:
    (A) LENGTH: 20 BASES
    (B) TYPE: NUCLEOTIDE
    (C) STRANDEDNESS: SINGLE
    (D) TOPOLOGY: LINEAR (ii) MOLECULE TYPE: DNA (ix) SEQUENCE DESCRIPTION: SEQ ID NO: 40:

GGGTTGAGAT GGAGACATTC                                        20

(2) INFORMATION FOR SEQ ID NO: 41:

(i) SEQUENCE CHARACTERISTICS:
    (A) LENGTH: 19 BASES
    (B) TYPE: NUCLEOTIDE
    (C) STRANDEDNESS: SINGLE
    (D) TOPOLOGY: LINEAR (ii) MOLECULE TYPE: DNA (xi) SEQUENCE DESCRIPTION: SEQ ID NO: 41:

AAGGGTGAGC TCTGTGTGC                                         19

(2) INFORMATION FOR SEQ ID NO: 42:

(i) SEQUENCE CHARACTERISTICS:
    (A) LENGTH: 20 BASES
    (B) TYPE: NUCLEOTIDE
    (C) STRANDEDNESS: SINGLE
    (D) TOPOLOGY: LINEAR (ii) MOLECULE TYPE: DNA ( x i ) SEQUENCE DESCRIPTION: SEQ ID NO: 42:

GGGTTGAGAT GGAGACATTC 20

( 2 ) INFORMATION FOR SEQ ID NO: 43:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 43:

GTCCCAGCTA CTCAGGACGC 20

( 2 ) INFORMATION FOR SEQ ID NO: 44:

( i ) SEQUENCE CHARACTERISTICS:
        ( A ) LENGTH: 23 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( i x ) SEQUENCE DESCRIPTION: SEQ ID NO: 44:

AGGAGTCTTT AATATGGACC CAG 23

( 2 ) INFORMATION FOR SEQ ID NO: 45:

( i ) SEQUENCE CHARACTERISTICS:
        ( A ) LENGTH: 20 BASES
        ( B ) TYPE: NUCLEOTIDE
        ( C ) STRANDEDNESS: SINGLE
        ( D ) TOPOLOGY: LINEAR     ( i i ) MOLECULE TYPE: DNA     ( x i ) SEQUENCE DESCRIPTION: SEQ ID NO: 45:

TGAGCCATGA TTGTGGCATA 20

METHOD FOR DETECTING POLYMORPHISM OF HUMAN CYTOCHROME P4501A2 GENE

TECHNICAL FIELD

The present invention relates to a method for diagnosing genes of drug metabolism-associated enzymes, and more particularly to a method for detecting polymorphism of the human cytochrome P4501A2 gene (hereinafter abbreviated as CYP1A2).

BACKGROUND ART

Human cytochrome P450 has important functions including detoxication and metabolic activation of drugs or exogenous materials and biosynthesis of steroid hormones and bile acid. CYP1A2 is one of the cytochrome P450 molecular species and is known to have a function of metabolizing drugs such as theophylline and phenacetin. The activity of CYP1A2 can be confirmed by a so-called caffeine test in which caffeine metabolites in urine after intake of coffee are quantitatively measured. It is known that the caffeine test has proved that there are poor metabolizers (hereinafter abbreviated as PMs) and extensive metabolizers (hereinafter abbreviated as EMs).

If a certain drug serves as a specific substrate for CYP1A2, it is considered that administration of the drug to PMs causes excessively strong effects (side effects) because PMs maintain high concentrations of the drug in blood. In fact, when theophylline is administered to PMs, about 30% of them are said to show side effects. To prevent side effects of this type which are manifested intensely due to polymorphism in drug metabolic activities, and if it is possible to distinguish extensive metabolizers and poor metabolizers by a gene diagnosis before administering a drug, better medicinal therapy directed to each patient can be achieved.

Similar polymorphism has been observed in other drug metabolizing enzymes such as CYP1A1, CYP2D6, and N-acetyltransferase. It is reported that the polymorphism of the drug metabolizing activity is attributed to gene polymorphism, and therefore, whether the patient is a PM or EM can be easily determined by gene diagnosis. However, with respect to CYP1A2, gene polymorphism has not yet been found.

The present invention clarifies a novel mutation of CYP1A2, and provides a new method for detecting gene polymorphism of CYP1A2.

DISCLOSURE OF THE INVENTION

The present inventors conducted an analysis of CYP1A2 genes of healthy human subjects and found a new polymorphism of the gene. They were also successful in developing a detection method therefor, leading to completion of the present invention.

Accordingly, the present invention provides a method for detecting polymorphism of the CYP1A2 gene characterized in that substitution at a 2064th base (mutation 1) present in a nontranslational region of the CYP1A2 gene is detected.

The present invention also provides a method for detecting polymorphism of the CYP1A2 gene characterized in that substitution at a 2640th base (mutation 2) present in a nontranslational region of the CYP1A2 gene is detected.

The present invention further provides a method for detecting polymorphism of CYP1A2 gene characterized in that deletion of a −1569th base (mutation 3) present in a nontranslational region of the CYP1A2 gene is detected.

BRIEF DESCRIPTION OF THE DRAWINGS

FIG. 1 shows the relation among types of gene polymorphism and the half life of theophylline in blood.

In FIG. 1, the ordinate represents the half life of theophylline and the abscissa represents types of gene polymorphism. Graph (A) and graph (B) show the results of detecting the 2640th polymorphism and −1549th polymorphism, respectively. The types of polymorphism shown in FIG. 1 are as follows:

C/C: homozygote of C
C/A: heterozygote of C and A
A/A: homozygote of A
T/T: homozygote of T
T/del: heterozygote of T and T-deletion
del/del: homozygote of T-deletion

BEST MODE FOR CARRYING OUT THE INVENTION

In the present invention, nucleotide sequences are expressed by symbols in accordance with definitions given by IUPAC-IUB and common names or common usage in the art. The nucleotide numbers of the above-mentioned mutation 1 and mutation 2 are expressed in accordance with CYP1A2 genome DNA (Mol. Endocrinol. 3 (9), 1399–1408 (1989)), and the nucleotide number of mutation 3 is expressed in accordance with CYP1A2 genome DNA (Mol. Pharmacol., 36 (1), 66–71 (1989)). The content of Mol. Endocrinol. 3 (9), 1399–1408 (1989) and Mol. Pharmacol., 36 (1), 66–71 (1989) are incorporated herein by reference.

The gene mutation elucidated by the present invention is characterized in that the 2064th base (T) and the 2640th base (C), both in the 5′-nontranslational region of CYP1A2 gene, are substituted by G and A, respectively, and that the −1569th base (T) is deleted. The present invention provides a new gene having at least one of these types of mutation.

The method of the present invention is characterized by detecting the above-mentioned specific types of mutation, and is useful in gene diagnosis for detecting CYP1A2 gene polymorphism. As long as the method is capable of detecting the aforementioned specific types of mutation which are clearly defined and characterized by the present invention, no limitation is imposed on the technique, etc. to be employed in the method. For example, a variety of routine methods may be widely used. Since the types of gene mutation to be detected by the present invention are now clarified and specified, it would be obvious for skilled persons in the art to adopt a suitable method, etc. for detecting them from the reading of the disclosure of this specification. Detection of the specific types of mutation according to the present invention encompasses detection of only one of the three types of mutation, detection of an arbitrary combination of two types, and detection of all the three types of mutation.

For example, the method of the present invention can be performed by analyzing the nucleotide sequences located in the above-specified positions. Such an analysis is within the scope of the present invention. Other methods which are advantageously employed include a method based on the physicochemical difference caused by mutation or difference in the site of restriction enzyme, for example, a method of utilizing the difference revealed in a variety of electrophoresis such as gel electrophoresis and capillary electrophoresis using a DNA sample containing one or more mutation points defined by the present invention; a method in which a suitable probe for detecting one or more mutation points of the present invention is used; and a combination of these methods. The probe for detecting mutation points is not particularly limited so long as it contains the aforementioned specific mutation points and assures a certain level of specificity in hybridization with a DNA sample to be tested so that the mutation points are detected. In general, the probe may be a DNA fragment constituted by a nucleotide sequence composed of dozens of bases, preferably 10–30 bases, including the mutation point(s) or its complementary DNA fragment.

More specifically, the detection method may be, for example, a Southern hybridization method or dot hybridization method (J. Mol. Biol., 98, 503–517 (1975), etc.), a PCR (polymerase chain reaction)–RFLP (restriction fragment length polymorphism) method, a PCR–SSCP (single strand conformation polymorphism) method (Proc. Natl. Acad. Sci., U.S.A., 86, 2766–2770 (1989), etc.), a PCR–SSO (specific sequence oligonucleotide) method, and a method combined with a DNA amplifying technique using a PCR method, for example, an ASO (allale specific oligomer) method in which a PCR–SSO method and dot hybridization method are employed (Nature, 324, 163–166 (1986), etc.). These methods may be used in combination. Particularly, a PCR method is recommended because it provides a simple and easy detection with high sensitivity and accuracy which requires only a small amount of a DNA sample.

Especially, in the present invention, an RFLP method is highly recommended due to its simplicity. Hereinafter, the present invention will be described in more detail taking an RFLP method as an example.

A variety of manipulations may be adopted in the detection method according to the present invention such as chemical synthesis of a partial DNA; treatment with enzymes for cleaving, deleting, adding, and combining of DNAs; and isolation, purification, duplication, and selection of DNAs can be performed according to conventional methods ("Experimental Techniques for Molecular Genetics", Kyoritsu Shuppan K.K., 1983; "PCR Technology", Takara Shuzo K.K., 1990; etc.). For example, isolation and purification of DNA may be performed by agarose gel electrophoresis, and DNA sequencing may be carried out by a dideoxy method (Proc. Natl. Acd. Sci., U.S.A., 74, 5463–5467 (1977), a Maxum-Gilbert method (Method in Enzymology, 65, 499–560 (1980)), etc. Sequencing of DNA nucleotides may also be easily performed by use of a commercially available sequencing kit. The PCR method for amplifying a certain region of DNA may also be performed according to conventional methods (e.g., Science, 230, 1350–1354 (1985)). These essential methods are adopted in the references cited in the present specification, and they will be referred to together with the examples described hereinafter.

In the detection method of the present invention, the genome DNA is detected in a sample of human origin, which is not limited so long as it contains genome DNA. For example, body fluids such as blood, marrow fluid, sperm, ascites, and urine; tissue cells such as a liver tissue; and body hair such as the hair. The genomic DNA can be prepared by extracting and purifying these samples.

From the genome DNA, a DNA region containing a mutation point of the present invention can be amplified to obtain a large amount of concentrated sample for testing. This type of example, i.e., a sample which is obtained by amplifying a DNA region containing a mutation point of the present invention, is particularly preferred as a material used in testing. Amplification may be performed, for example, in accordance with a PCR method using a primer which is suitably designed so as to amplify only part of a nontranslational region containing polymorphism. Such a primer can be prepared by conventional methods. No limitation is imposed on the base length of the region to be amplified, etc. In ordinary situations, the base length is approximately 100 bp to 500 bp. A preferable example of a primer thus prepared will be specifically described in the section of Examples hereinafter. When a primer is prepared in accordance with the description of the present invention, suitable samples for testing can be obtained as amplified DNA fragments each containing one polymorphous segment and having a specific length.

In performing a PCR–RFLP method, the DNA which will be amplified is designed to include an arbitrary enzymatic site which can be suitably used in the subsequent RFLP method. No limitation is imposed on such designing so long as the length of a fragment obtained by cleavage of the DNA region with an enzyme differs in two cases of a mutation gene and wild type gene. A restriction enzyme site which is generated or lost by the mutation of the present invention may be used. If bases which have been varied do not serve as the sites recognized by restriction enzymes when they are used solely, desired restriction enzyme sites can be artificially introduced by placing a mismatch in a primer.

Thus, a desired DNA region which has been amplified according to a PCR method is digested by a restriction enzyme suitably selected as described above. The fragments resulting from cleavage are confirmed by electrophoresis as they show specific bands.

Based on band patterns obtained in the above procedure, CYP1A2 gene polymorphism (presence of a mutation according to the present invention) can be detected. This is useful in gene diagnosis of polymorphism in metabolic activity of diverse drugs which serve as specific substrates for the CYP1A2 gene.

In performing the gene diagnosis of the present invention, it is preferable that a diagnosis agent containing, as active components, means or reagents for detecting the presence of a type of mutation according to the present invention are employed. Accordingly, the present invention also provides a diagnosis agent for detecting polymorphism in metabolic activity of a drug which is pertinent to the CYP1A2 gene. The diagnosis agent contains, as an essential component, a specific reagent corresponding to the method which is used for detecting a type of mutation of the present invention. The specific reagent is suitably selected in accordance with the detection method adopted. A characteristic feature of the reagent is that it is necessary to constitute means for detecting a type of mutation defined by the present invention, e.g., the DNA fragments and/or specific restriction enzymes serving as probes for detection. Reagents such as specifically prepared primers for use in a PCR amplification step for specifically amplifying regions containing mutation points of the present invention are not considered essential components of the diagnosis agent of the invention. They may also be included in the diagnosis agent of the present invention alike reagents for performing hybridization.

EXAMPLES

The present invention will further be described in more detail by way of examples, which should not be construed as limiting the invention.

The symbols representing the reagents used in the following examples are as follows. When needed, some reagents were sterilized in an autoclave (121° C., 20 minutes).

EDTA: Ethylenediaminetetraacetate•2Na

SDS: Sodium dodecylsulfate

TE: 10 mM Tris-HCl (pH 7.5), 1 mM EDTA (pH 8.0)

10×PCR buffer: 100 mM Tris-HCl (pH 8.3), 500 mM KCl, 15 mM magnesium chloride, 0.01% (w/v) gelatin dNTP: Deoxynucleotide triphosphate Formamide pigment: 95% deionized formamide, 0.05% Blue dextran LB medium: Trypton (10 g), NaCl (10 g), and yeast extract (5 g) are dissolved in purified water to make a total amount 1 liter.

LBamp medium: A medium obtained by adding ampicillin to the above medium so as to have a final concentration of 50 μ/ml LBamp plate: A medium obtained by adding 15 g agar powder to the above LBamp medium ddNTP: Dideoxynucleoside triphosphate APS: Ammonium persulfate 10×TBE: Tris (108 g), boric acid (55 g), and EDTA-2Na (9.3 g) are dissolved in purified water to make a total amount 1 liter.

Example 1

Analysis of Nucleotide Sequence of CYP1A2 Mutated Gene (1) Genomic DNAs were prepared using human peripheral blood in accordance with the following method. 10 ml of human peripheral blood collected in the presence of an anti-coagulant EDTA was subjected to centrifugal separation at 2,500 rpm for 30 minutes to remove the serum. Subsequently, 0.2% NaCl solution was added to make a total amount 50 ml. The solution was nonviolently shaken 5-6 times, and allowed to stand on ice for 15 minutes. Thereafter, it was subjected to centrifugal separation at 2,500 rpm for 30 minutes, thereby collecting pellets. Using a 0.2% NaCl solution, another washing was performed in a manner similar to the previous one. To thus-obtained pellets, 10 mM of Tris-HCl (pH 8.0) and 10 mM EDTA (4 ml) were added to suspend the pellets. 10% SDS, 25 mg/ml of proteinase K, and 10 mg/ml of RNase A were added to the suspension in amounts of 4 ml, 16 μl, and 20 μl, respectively, followed by lightly mixing by turning the suspension upside down. Thereafter, the suspension was incubated at 37° C. overnight.

Next, 4 ml of a phenol/Tris solution was added and the resulting mixture was mixed by turning the mixture upside down. A centrifugal separation at 3,000 rpm for 10 minutes was performed to recover an aqueous layer. The aqueous layer was combined with 4 ml of a phenol/chloroform solution, followed by inversive mixing and centrifugal separation at 3,000 rpm for 10 minutes. An aqueous layer was recovered. Finally, extraction with chloroform was conducted twice to obtain an aqueous phase, to which a one-tenth in amount of 3M sodium acetate (pH 5.2) and cold ethanol in twice the amount were added to allow DNAs to settle. The thus-obtained DNAs were washed with 70% ethanol to obtain genomic DNAs. The genomic DNAs were dissolved in a TE solution and then the mixture was submitted to a quantitative determination in which absorption at 260 nm was measured.

(2) PCR-SSCP analysis (a) Determination of a primer

All the exons and exon-introns of a CYP1A2 gene were divided into eleven. The nontranslational region which is located at about 900 bp upstream of the translation initiation point of the CYP1A2 gene was divided into six, and primers each specifically amplifying each of the six fragments were determined. Primers were synthesized using a DNA synthesizing apparatus (Pharmacia LKB Gene Assembler Plus).

The nucleotide sequences of the primers are shown below. (Primer pairs for exons and exon-introns).

F1: 5'-CCTCCTTTTTTCCCTGCAGT-3' (SEQ ID NO:1)

R1: 5'-TCATCCTTGACAGTGCCAGG-3' (SEQ ID NO:2)

F2: 5'-ATGTGCTGACCCTGGGGAA-3' (SEQ ID NO:3)

R2: 5'-GCTGAAGGTCAAGCTCTGG-3' (SEQ ID NO:4)

F3: 5'-CCTCCACCCTCATCACTGA-3' (SEQ ID NO:5)

R3: 5'-TGTAAGGGTCGAAGTGCCC-3' (SEQ ID NO:6)

F4: 5'-TGCAGGAGCTGATGGCAGG-3' (SEQ ID NO:7)

R4: 5'-CGAAGGATGGGGAAGAAGT-3' (SEQ ID NO:8)

F5: 5'-TCATGAGTTCGTGGAGACTG-3' (SEQ ID NO:9)

R5: 5'-AAGGTGCCCCTTGCCACC-3' (SEQ ID NO:10)

F6: 5'-AGTGCCAGAGTGCCCCTAA-3' (SEQ ID NO:11)

R6: 5'-TGAACAGCAGGCATGTGGAT-3' (SEQ ID NO:12)

F7: 5'-TCCTCACCTTACACTACAGG-3' (SEQ ID NO:13)

R7: 5'-TGGGTTTCAAGGCTTCTCCT-3' (SEQ ID NO:14)

F8: 5'-CTGCTTGTCCTCTGTGTTCT-3' (SEQ ID NO:15)

R8: 5'-TGGCAAGCACTTTAGAGGTG-3' (SEQ ID NO:16)

F9: 5'-GCAACACATGCCCCAGCTT-3' (SEQ ID NO:17)

R9: 5'-ACTGCTGAACCTGCACACAT-3' (SEQ ID NO:18)

F10: 5'-ATCTCCTGCTGTTCCTCTTG-3' (SEQ ID NO:19)

R10: 5'-AACTCCAGTTGCTGTAGCAG-3' (SEQ ID NO:20)

F11: 5'-CCAAGTGGGAGATCTTCCTC-3' (SEQ ID NO:21)

R11: 5'-GGAAGAGAAACAAGGGCTGA-3' (SEQ ID NO:22)

(Primer pairs for 5'-nontranslational regions)

5' F1: 5'-AACCAGGCCAATCTGATAGG-3' (SEQ ID NO:23)

5' R1: 5'-AGCTTCCAGGTTCTATAGTTG-3' (SEQ ID NO:24)

5' F2: 5'-GTACCTTTCTTGGGACCAAT-3' (SEQ ID NO:25)

5' R2: 5'-AATGGCTTAGTCCAAACTGC-3' (SEQ ID NO:26)

5' F3: 5'-CTACCCAGCTCTTGACTTCT-3' (SEQ ID NO:27)

5' R3: 5'-CAGGGCATTCTTTATCAATA-3' (SEQ ID NO:28)

5' F4: 5'-GTGAGAGGATGGGGACTCAT-3' (SEQ ID NO:29)

5' R4: 5'-GTACCAAAGAGTCCCTGCCA-3' (SEQ ID NO:30)

5' F5: 5'-CCCTTGGGTATATGGAAGGT-3' (SEQ ID NO:31)

5' R5: 5'-CAACATGAACGCTGGCTCT-3' (SEQ ID NO:32)

5' F6: 5'-CCCAGAAGTGGAAACTGAGA-3' (SEQ ID NO:33)

5' R6: 5'-GGGTTGAGATGGAGACATTC-3' (SEQ ID NO:34)

(b) Amplification of exons and exon-introns as well as 5'-nontranslational regions of the CYP1A2 gene by PCR:

Exons and exon-introns as well as 5'-nontranslational regions of the CYP1A2 gene were amplified by PCR as described below.

Briefly, to 100 ng of a genomic DNA solution prepared in the step (1) above, 5 μl of a 10×PCR buffer, 4 μl of 10 mM dNTP, 1.25 units of Taq DNA polymerase, and 50 pmol of each primer described in the step (a) above were added. Further, purified water was added to make a total volume 50 μl. Finally, mineral oil was placed on the resulting mixture. Forty cycles of a reaction consisting of 95° C.–1 min., 58° C.–1.5 min., and 72° C.–1.5 min. were performed. After completion of the reaction, 10 μl of each PCR reaction liquid was subjected to 7.5% polyacrylamide gel electrophoresis. A single band was obtained.

(c) PCR–SSCP analysis

To 10 μl of the thus-obtained PCR reaction liquid, 10 μl of a formamide pigment was added. The mixture was denatured with heat at 95° C. for 5 minutes. Immediately thereafter, the mixture was cooled on ice to form a single strand DNA. Its entire amount was subjected to 7.5% polyacrylamide gel electrophoresis with constant current of 15 mA. 2 μg/ml of ethidium bromide was used as a staining substance.

(3) Subcloning of a region with polymorphism and analysis of its nucleotide sequence A single stranded DNA band having a mobility different from others was cut out, which was detected as a result of the PCR–SSCP procedure described in (2)-(c) above, and soaked in 50 μl of TE, followed by a mixing of 5 minutes. 5 μl of its supernatant was subjected to PCR amplification using a primer same as that used above to form a double stranded DNA. 1 μl of a PT7 Blue-T vector (product of Novagen), 12 μl of Liquid A of a DNA ligation kit (product of Takara Shuzo), and 3 μl of Liquid B of the DNA ligation kit (product of Takara Shuzo) were added to 1 μl of a PCR reaction liquid and mixed. The mixture was incubated at 16° C. for 12 hours to effect ligation. 1 μl of the mixture was taken and combined with 20 μl of JM 109 competent cells (product of Takara Shuzo). The resulting mixture was allowed to stand for 30 minutes on ice, then a heat shock of 42° C. for 45 seconds was applied. 80 μl of an LB medium was added and incubated at 37° C. for 1 hour. On an LBamp plate, culturing at 37° C. over night yielded a transformant.

Colonies of the transformant were recovered and cultured on 3 μl of an LBamp medium. Thereafter, a small amount of plasmid DNA was prepared following the instructions given in a manual accompanying Plasmid Pureprep Kit (product of Takara Shuzo). 30 μl of a plasmid DNA solution was obtained. Part of the solution (5 μl) was subjected to a digestion step using restriction enzymes BamHI and PstI so as to sandwich the cloning site. Electrophoresis with 3% agarose gel confirmed that the target DNA fragment was inserted.

The nucleotide sequence of the clone thus obtained was analyzed by first performing a sequencing reaction with an Autocycle Sequencing Kit (product of Pharmacia) and then determining the nucleotide sequence by electrophoresis and data analysis using a DNA Auto Sequencer (ALF DNA Sequencer, product of Pharmacia).

(4) Results of the analysis

A PCR–SSCP analysis conducted on samples from 60 healthy humans with respect to exons and exon-introns of the CYP1A2 gene could not confirm gene polymorphism. However, in the 5'-nontranslational region of CYP1A2, 2 fragments were confirmed which had a mobility different from other fragments, i.e., which contained points of mutation.

When the nucleotide sequence of these fragments was analyzed, it was found that the 2064th base and 2640th base were shifted from T to G and from C to A, respectively.

Example 2

Detection of polymorphism of CYP1A2 gene by PCR-–RFLP (1) Determination of a primer Four kinds of primer pairs were designed depending on the type of polymorphism of the 2064th and 2640th bases in the 5'-nontranslational region so as to permit digestion with a restriction enzyme after PCR amplification. When varied bases alone were not enough to serve as the sites to be recognized by restriction enzymes, a mismatch was placed in the primer to artificially introduce recognition sites for restriction enzymes.

The nucleotide sequences of the primer pairs thus designed are shown below.

2064TF: 5'-GAGCCTGGGCTAGGTGACGGGG-3' (SEQ ID NO:35)

2064TR: 5'-GGCTGCCCTTGTGCTAAG-3' (SEQ ID NO:36)

2064GF: 5'-AAAGACGGGGAGCCTGGGCTAGGTG-3' (SEQ ID NO:37)

2064GR: 5'-AGCCAGGGCCAGGGCTGCCCTTGTGCTAAG-3' (SEQ ID NO:38)

2640CF: 5'-CCCAGAAGTGGAAACTGAGA-3' (SEQ ID NO:39)

2640CR: 5'-GGGTTGAGATGGAGACATTC-3' (SEQ ID NO:34)

2640 AF: 5'-AAGGGTGAGCTCTGTGTGC-3' (SEQ ID NO:40)

2640AR: 5'-GGGTTGAGATGGAGACATTC-3' (SEQ ID NO:34)

(2) Amplification of the 5'-nontranslational region of the CYP1A2 gene by PCR

To 500 ng of a genomic DNA solution prepared in step (1) of Example 1, 5 μl of a 10×PCR buffer, 4 μl of 10 mM dNTP, 1.25 units of Taq DNA polymerase, and 50 pmol of each of the four sense primers and antisense primers described in the step (1) above were added. Further, purified water was added to make a total volume 50 μl. Finally, mineral oil was placed on the resulting mixture. Forty cycles of a reaction consisting of 95° C.–1 min., 58° C.–1.5 min., and 72° C.–1.5 min. were performed. After completion of the reaction, the PCR reaction liquid was subjected to 7.5% polyacrylamide gel electrophoresis. A single band was obtained.

(3) Determination of polymorphism of the 5'-nontranslational region of the CYP1A2 gene by treating a PCR reaction product with a restriction enzyme To 10 μl of a PCR reaction product amplified in step (2) above, 1 μl of a buffer for restriction enzyme reaction and 1 μl of a restriction enzyme were added and digested at 37° C.

overnight. Thereafter, electrophoresis was conducted using 7.5% polyacrylamide gel. Polymorphism was determined as follows.

Briefly, PCR was conducted using 2064TF and 2064 TR as a sense primer and an antisense primer, respectively. As a result, a fragment of 148 bp was amplified. The fragment was treated with a restriction enzyme AspI. Genes in which the 2064th base was T showed bands of 129 bp and 19 bp, whereas genes in which the 2064th base was G showed a band of 148 bp.

Similarly, in PCR where 2064GF and 2064 GR were used as a sense primer and an antisense primer, respectively, a fragment of 169 bp was amplified. When this fragment was treated with a restriction enzyme StuI, genes in which the 2064th base was T showed a band of 169 bp, whereas genes in which the 2064th base was G showed bands of 137 bp and 32 bp.

Moreover, in PCR where 2640CF and 2640 CR were used as a sense primer and an antisense primer, respectively, a fragment of 243 bp was amplified. When this fragment was treated with a restriction enzyme ApaI, genes in which the 2640th base was C showed bands of 124 bp and 119 bp, whereas genes in which the 2640th base was A showed a band of 243 bp.

Similarly, in PCR where 2640AF and 2640 AR were used as a sense primer and an antisense primer, respectively, a fragment of 145 bp was amplified. When this fragment was treated with a restriction enzyme ApaLI, genes in which the 2640th base was C showed a band of 145 bp, whereas genes in which the 2640th base was A showed bands of 129 bp and 16 bp.

From the above results, polymorphism of the CYP1A2 gene can be determined.

Example 3

In a manner similar to that described in Example 1, a nontranslational region on an even more upstream side compared to the region studied in Example 1 was divided into 18 fragments. Primers which specifically amplified them were designed. All the regions of the CYP1A2 gene were studied.

As a result, fragments containing points of mutation were found which were in the regions amplified by primer pairs of 5'10F (5'-GTCCCAGCTACTCAGGACGC-3') (SEQ ID NO:41) and 5'10R (5'-AGGAGTCTTTAATATGG ACCCAG-3') (SEQ ID NO:42).

Analysis of the nucleotide sequence of these fragments confirmed a point of mutation where −1569th base T was deleted.

Example 4

Detection of polymorphism at the −1569th base of the CYP1A2 gene by PCR-RFLP

In accordance with the type of polymorphism at the −1569th base in the 5'-nontranslational region where polymorphism is present, primer pairs were designed so as to permit digestion with a restriction enzyme after undergoing PCR amplification. When varied bases alone were not enough to serve as the sites to be recognized by restriction enzymes, a mismatch was placed in the primer to artificially introduce recognition sites for restriction enzymes.

The nucleotide sequences of the primer pairs thus designed are shown below.

−1569TF: 5'-TGAGCCATGATTGTGGCATA-3' (SEQ ID NO:43)

−1569TR: 5'-AGGAGTCTTTAATATGGACCCAG-3' (SEQ ID NO:42)

In a manner similar to that described in Example 2, PCR amplification was performed and polymorphism was determined by treating the PCR reaction product using a restriction enzyme.

Briefly, by PCR amplification, a fragment of 167 bp was amplified. When this fragment was treated with a restriction enzyme NdeI, genes in which the −1569th base was T showed bands of 148 bp and 19 bp, whereas genes in which the −1569th base was deleted showed a band of 167 bp.

Thus, gene polymorphism of this position can be determined.

Example 5

Distribution of CYP1A2 gene polymorphism in healthy humans

The procedure described in Examples 2 and 4 was followed to determine gene polymorphism of 52 healthy humans.

As a result, among 52 individuals who had polymorphism at the 2064th base, 46 were found to have a homozygote of T (88%), 5 were found to have a heterozygote of T and G (10%), and 1 was found to have a homozygote of G (2%).

Moreover, among 51 individuals who had polymorphism at the 2640th base, 6 were found to have a homozygote of C (12%), 33 were found to have a heterozygote of C and A (64%), and 12 were found Go have a homozygote of A (24%).

Furthermore, among 40 individuals who had polymorphism at the −1569th base, 14 were found to have a homozygote of T (35%), 20 were found to have a heterozygote of T and T-deletion (50%), and 6 were found to have a homozygote of T-deletion (15%).

Example 6

Theophylline metabolism and CYP1A2 gene polymorphism in patients who were given theophylline In 32 patients who needed theophylline and to whom theophylline preparations were continuously dosed for at least 4 days in order for the steady state of the theophylline concentration in blood to secure, ability of metabolizing theophylline (half life: T½ (hr)) was calculated using the blood theophylline concentration (Journal of Pharmacokinetics and Biopharmaceutics, 22 (1), 59–71 (1994)).

Separately, gene polymorphism was studied in accordance with Examples 2 and 4 on the genomic DNA prepared from peripheral blood in accordance with Example 1.

Figure 1A:
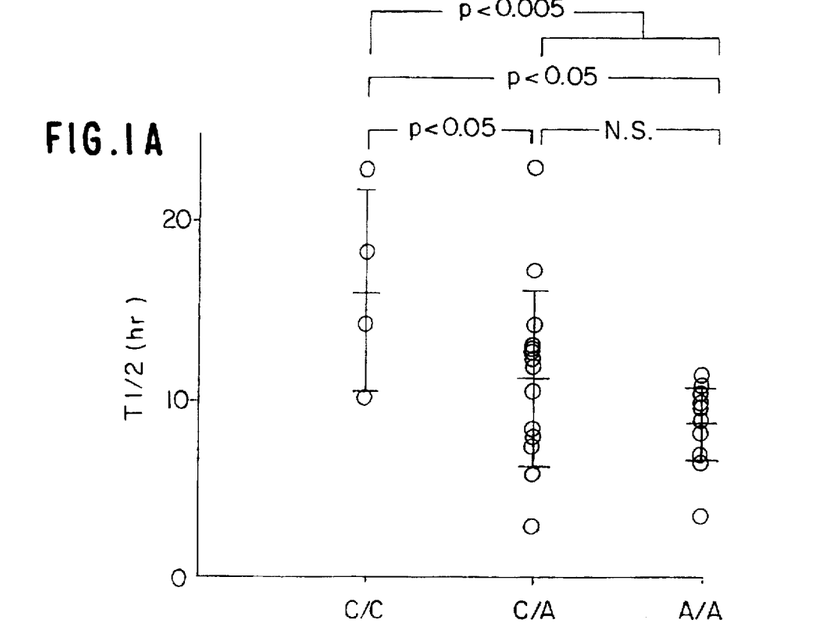
Figure 1B:
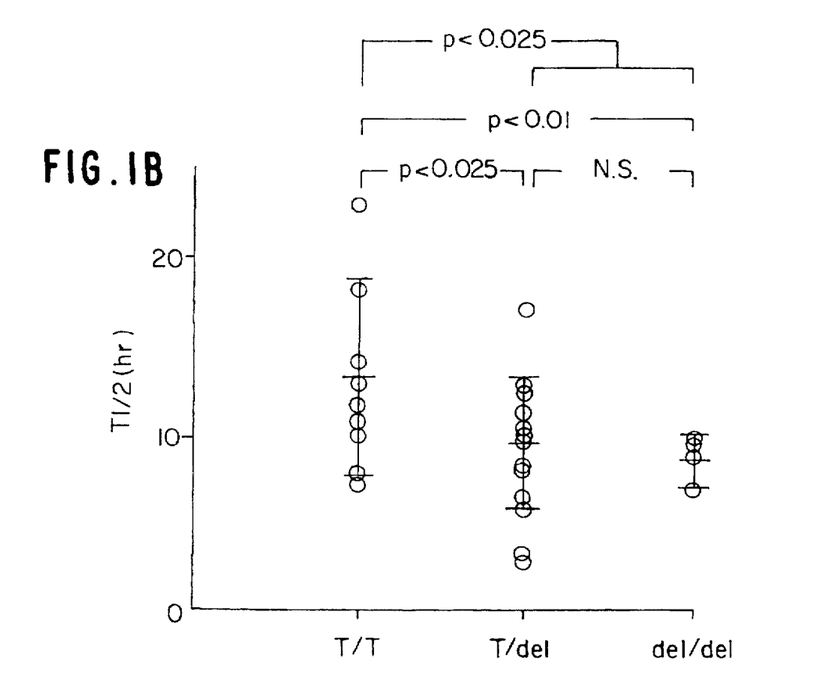

The results are shown in FIG. 1(A) and FIG. 1(B).

From the drawings, it is understood that the gene polymorphism at the 2640th and −1569th bases is correlated with the metabolic activity of theophylline in a statistically significant manner. That is, it is understood that when the 1640th base is C, metabolism is meaningfully slowed down, and when the base is A, metabolism is meaningfully accelerated, and moreover, when the −1569th base is T, metabolism is meaningfully slowed down, and when the base is lost, metabolism is meaningfully accelerated. No correlation was found between the 2064 polymorphism and the metabolic activity of theophylline As described above, it is concluded that the 2640th and −1569th polymorphism in the CYP1A2 gene causes polymorphism in metabolic activity of theophylline. Therefore, detection of such polymorphism in accordance with the present invention is useful for performing a gene diagnosis when theophylline is administered to the patient.

INDUSTRIAL UTILITY

The present invention elucidated new points of mutation of the CYP1A2 gene and provides a method for detecting the novel gene polymorphism of CYP1A2. Moreover, according to the present invention, only a small amount of a DNA sample is enough to detect the novel polymorphism of the CYP1A2 gene. The detection is simple and easy, and provides high sensitivity and high accuracy. As a result, the invention provides a gene diagnosis for detecting polymorphism in metabolic activity of theophylline or similar substances.

---

What is claimed is:

1. A method for detecting a polymorphism of the human cytochrome P4501A2 gene comprising:
   a) isolating a nucleic acid sample;
   b) combining said nucleic acid sample with either a probe or a primer pair; and
   c) determining whether a substitution has occurred at position 2064 of said human cytochrome P4501 A2 gene.

2. The method according to claim 1, wherein the substitution is from T to G.

3. The method according to claim 1, wherein the method for detecting polymorphism of the human cytochrome P4501A2 gene is a PCR-RFLP method.

4. The method according to claim 1, further comprising the further step of:
   (d) determining the metabolic activity of a drug in a host on the basis of whether said substitution has occurred.

5. The method according to claim 4, wherein the drug is theophylline.

6. A method for detecting a polymorphism of the human cytochrome P4501A2 gene comprising:
   a) isolating a nucleic acid sample;
   b) combining said nucleic acid sample with either a probe or a primer pair; and
   c) determining whether a substitution has occurred at position 2640 of said human cytochrome P4501A2 gene.

7. The method according to claim 6, wherein the substitution is from C to A.

8. The method according to claim 6, wherein the method for detecting polymorphism of the human cytochrome P4501A2 gene is a PCR-RFLP method.

9. The method according to claim 6, further comprising the further step of:
   (d) determining the metabolic activity of a drug in a host on the basis of whether said substitution has occurred.

10. The method according to claim 9, wherein the drug is theophylline.

11. A method for detecting a polymorphism of the human cytochrome P4501A2 gene comprising:
   a) isolating a nucleic acid sample;
   b) combining said nucleic acid sample with either a probe or a primer pair; and
   c) determining whether a substitution has occurred at position −1569 of said human cytochrome P4501A2 gene.

12. The method according to claim 11, wherein the method for detecting polymorphism of the human cytochrome P4501A2 gene is a PCR-RFLP method.

13. The method according to claim 11, further comprising the further step of:

(d) determining the metabolic activity of a drug in a host on the basis of whether said substitution has occurred.

14. The method according to claim 13, wherein the drug is theophylline.

* * * * *